(12) United States Patent
Tulkki

(10) Patent No.: US 7,222,539 B2
(45) Date of Patent: May 29, 2007

(54) SENSOR AND GUIDE WIRE ASSEMBLY

(75) Inventor: Sauli Tulkki, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 88 days.

(21) Appl. No.: 11/144,624

(22) Filed: Jun. 6, 2005

(65) Prior Publication Data
US 2005/0268725 A1    Dec. 8, 2005

Related U.S. Application Data

(60) Provisional application No. 60/576,603, filed on Jun. 4, 2004.

(51) Int. Cl.
*G01L 7/00* (2006.01)
(52) U.S. Cl. ...................................... 73/756
(58) Field of Classification Search ............. 73/756, 73/706, 719; 604/101; 128/675
See application file for complete search history.

(56) References Cited

U.S. PATENT DOCUMENTS

| | | | |
|---|---|---|---|
| 4,771,782 A | 9/1988 | Millar | |
| 4,878,898 A * | 11/1989 | Griffin et al. | ............ 604/96.01 |
| RE36,648 E | 4/2000 | Uber, III et al. | |
| 6,112,598 A | 9/2000 | Tenerz et al. | |
| 6,167,763 B1 * | 1/2001 | Tenerz et al. | ............... 73/756 |
| 6,224,585 B1 | 5/2001 | Pfeiffer | |
| 2002/0143251 A1 * | 10/2002 | Richardson et al. | ......... 600/434 |
| 2005/0000294 A1 | 1/2005 | Tenerz et al. | |
| 2005/0011272 A1 | 1/2005 | Tenerz | |

FOREIGN PATENT DOCUMENTS

JP     2003-265617 A     9/2003

* cited by examiner

*Primary Examiner*—Jewel Thompson
(74) *Attorney, Agent, or Firm*—Foley & Lardner LLP

(57) ABSTRACT

The invention relates to a sensor and guide wire assembly (20) for intravascular measurements of physiological variables in a living body, comprising a core wire (21) and a sensor element (22). The sensor and guide wire assembly (20) comprises further a jacket (25; 35; 45) provided with a first opening (26; 36; 46), in which at least a portion of the sensor element (22) is arranged, and a second opening (27; 37; 47), in which a portion of the core wire (21) is arranged, the first opening (26; 36; 46) and the second opening (27; 37; 47) being separated from each other.

23 Claims, 4 Drawing Sheets

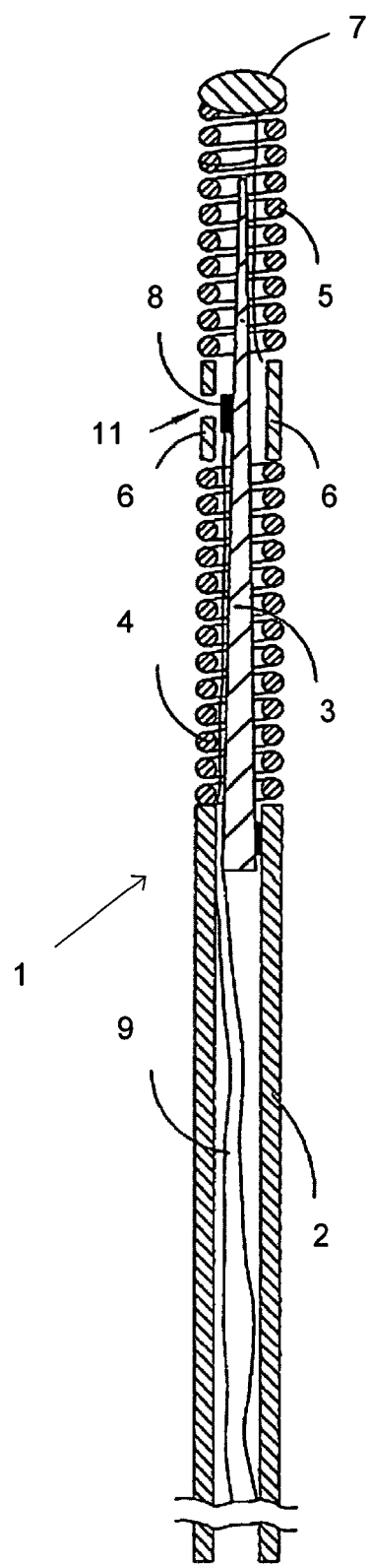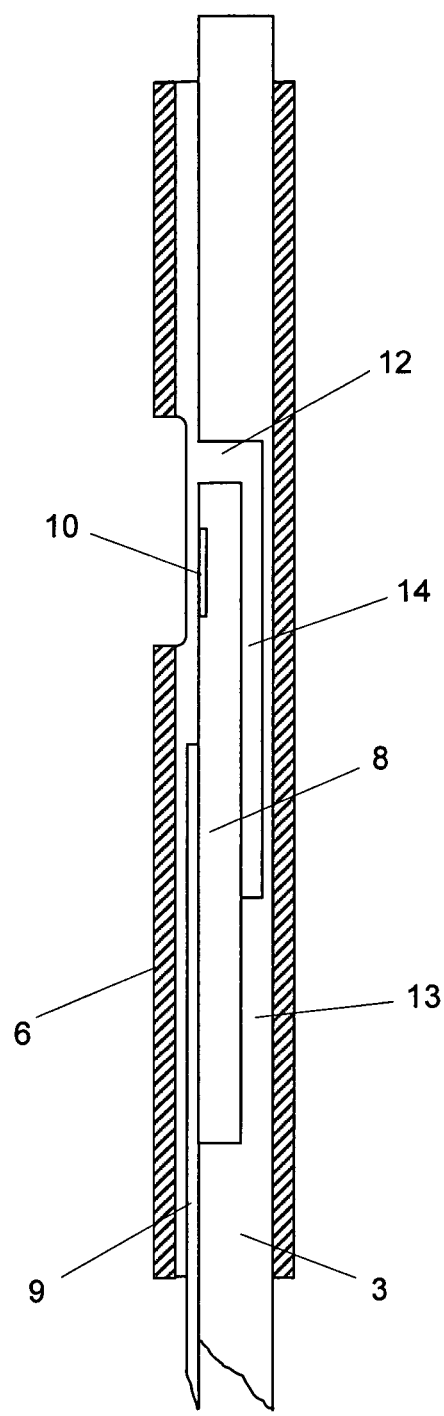
Fig. 1
(Prior Art)
Fig. 2
(Prior Art)

SENSOR AND GUIDE WIRE ASSEMBLY

FIELD OF THE INVENTION

The present invention relates generally to sensor and guide wire assemblies, in which a sensor element is mounted at the distal end of a guide wire for intravascular measurements of physiological variables in a living body, and in particular to the mounting arrangement of the sensor element.

BACKGROUND OF THE INVENTION

Sensor and guide wire assemblies in which a sensor is mounted at the distal end of a guide wire are known. In U.S. Pat. No. Re. 35,648, which is assigned to the present assignee, an example of such a sensor and guide wire assembly is disclosed, where a sensor guide comprises a sensor element, an electronic unit, a signal transmitting cable connecting the sensor element to the electronic unit, a flexible tube having the cable and the sensor element disposed therein, a solid metal wire, and a coil attached to the distal end of the solid wire. The sensor element comprises a pressure sensitive device, e.g. a membrane, with piezoresistive elements connected in a Wheatstone bridge-type of arrangement mounted thereon.

As is recognized in U.S. Pat. Nos. 6,112,598 and 6,167,763, which also are assigned to the present assignee, a potential problem with this kind of guide wire mounted sensor is the occurrence of so-called bending artefacts. A bending artefact is a change in the output signal from the sensor that is induced by a bending of the guide wire, rather than being induced by a change in the physical environment surrounding the sensor. For a sensor and guide wire assembly like the one disclosed in U.S. Pat. No. Re. 35,648, this means that when the guide wire is bent, the bending of the guide wire imposes a strain on the sensor element, which thereby is deflected or stretched (or contracted). The deflection of the sensor element is then transferred to a deformation of the pressure sensitive device; and, according to well-known principles, the output from the Wheatstone bridge will thereby be affected by the bending of the guide wire.

According to U.S. Pat. Nos. 6,112,598 and 6,167,763, a solution to this problem is to mount the sensor element in a cantilevering fashion such that the pressure sensitive end of the sensor element does not contact any structure other than its mount. These two patents disclose several embodiments with different ways of mounting the sensor element such that bending forces are not exerted on the pressure sensitive end of the sensor element. A common feature of these embodiments is that an elongated, essentially rectangular sensor chip is mounted in a recess in the core wire in such a way that the proximal end of the chip is attached to the core wire, while the distal end of the sensor chip protrudes into the recess such that a clearance is provided below the distal portion of the chip where the pressure sensitive device (e.g. a membrane) is provided.

In the U.S. patent application Ser. No. 10/611,661, which is assigned to the present assignee, a clearance is also provided below the distal portion of the sensor chip, but here the chip has been provided with an extra mounting base, which at a proximal portion of the sensor chip protrudes downwards for mounting to the core wire and which thereby creates a clearance below a distal portion of the chip.

A principally different solution to the bending artefact problem is presented in the U.S. patent application Ser. No. 10/622,136, which also is assigned to the present assignee. Here the sensor chip is provided with a recess, which will act as a hinge or articulation when the core wire is bent. By the provision of this articulated portion, the pressure sensitive portion of the sensor element is not constrained to adapt to bending deformations of the core wire, which prevents such deformations from being transferred to the pressure sensitive device.

The entire contents of all of the above-described documents are incorporated herein by reference.

Although sensor and guide wire assemblies provided with sensor chips designed and mounted according to the different teachings of the above-listed documents in practise have proven to work well, the design of a sensor and guide wire assembly can be improved, not least from a manufacturing point of view.

SUMMARY OF THE INVENTION

A sensor element of a sensor and guide wire assembly comprises an elongated, essentially rectangular chip with a pressure sensitive member in the form of a membrane made from polysilicon provided thereon. This sensor chip is arranged in a short tube, also referred to as a jacket or sleeve. According to the prior art, the jacket is hollow and accommodates besides the sensor chip also a portion of a core wire and at least one electrical lead connected to the pressure sensitive member. In order to protect and fixate the sensor element and the core wire inside the jacket, the jacket can also be filled with a suitable material such as silicone.

An object of the present invention is to provide a new and improved design for a jacket or sleeve, which is a member of a sensor and guide wire assembly, in such a way that, when a sensor chip is mounted in the jacket or sleeve, the sensor and guide wire assembly will have the same or better characteristics regarding resistance against bending artefacts. Preferably, the sensor and guide wire assembly should at the same time be easier and thereby cheaper to manufacture.

These objects are achieved with a sensor chip and a sensor and guide wire assembly according to the present invention.

According to the invention, a sensor and guide wire assembly comprises a sensor element in the form of a generally rectangular and rather thin sensor chip having a pressure sensitive device provided thereon. The pressure sensitive device can be in the form of a membrane, which covers a small recess in the upper side at a first end of the sensor chip and which has piezoresistive elements mounted thereon. The sensor element is disposed in a first separate longitudinal opening or hole in a jacket or sleeve. The jacket or sleeve comprises further a second separate longitudinal opening or hole, in which a portion of a core wire is accommodated.

By arranging the sensor chip and the core wire in separate compartments in a jacket, the sensor chip is virtually independent of movements of the core wire; and in particular bending deformations of the core wire will not be transferred to the sensor chip. By this arrangement, it is not necessary to provide the core wire with a special mounting structure, such as a recess or a flattened portion. In comparison with sensor and guide wire assemblies according to the prior art, this arrangement allows the manufacturing of a sensor and guide wire assembly to be made simpler and cheaper.

In a first embodiment of a jacket according to the present invention, the longitudinal opening for accommodating a sensor chip is cylindrical, whereas the longitudinal opening has been given a rectangular cross-section in a second embodiment of the invention. In a third embodiment, separate openings for respectively the sensor chip and the core wire have been accomplished by a partition wall that divides the interior of a jacket into two semi-circular compartments.

BRIEF DESCRIPTION OF THE DRAWINGS

FIG. 1 illustrates schematically the general design of a sensor and guide wire assembly according to the prior art.

FIG. 2 illustrates an example of a mounting arrangement for the sensor element of the sensor and guide wire assembly shown in FIG. 1.

DETAILED DESCRIPTION OF THE INVENTION

Figure 3:
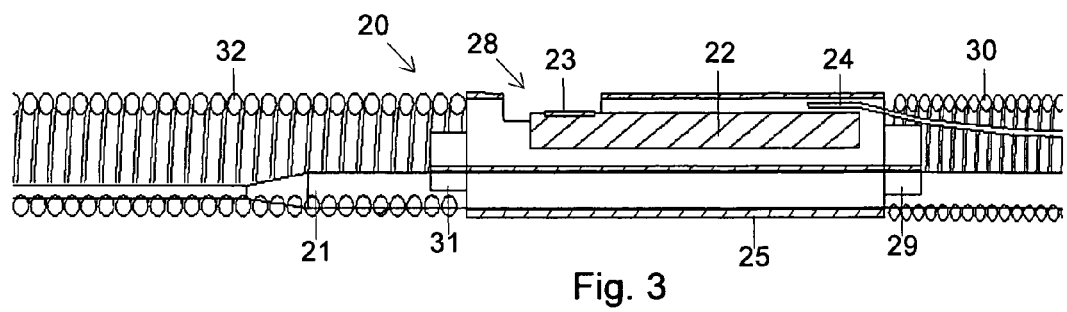
FIG. 3 illustrates a portion of a sensor and guide wire assembly comprising a jacket according to the present invention.

For better understanding of the context in which the present invention is going to be used, a sensor and guide wire assembly 1 of a conventional design is illustrated in FIG. 1. The sensor guide 1 comprises a hollow tube 2, a core wire 3, a first coil 4, a second coil 5, a jacket or sleeve 6, a dome-shaped tip 7, a sensor element or chip 8, and one or several electrical leads 9. The proximal end of the first coil 4 is attached to the distal end of the hollow tube 2, while the distal end of the first coil 4 is attached to the proximal end of the jacket 6. The proximal end of the second coil 5 is connected to the distal end of the jacket 6, and the dome-shaped tip 7 is attached to the distal end of the second coil 5. The core wire 3 is at least partly disposed inside the hollow tube 2 such that the distal portion of the core wire 3 extends out of the hollow tube 2 and into the second coil 5. The sensor element 8 is mounted on the core wire 3 at the position of the jacket 6, and is through the electrical leads 9 connected to an electronic unit (not shown in the figure). The sensor element 8 comprises a pressure sensitive device in the form of a membrane 10 (not visible in the figure), which through an aperture 11 in the jacket 6 is in contact with a medium, such as blood, surrounding the distal portion of the sensor guide 1.

Although not shown in the figure, the sensor element 8 further comprises an electrical circuitry, which in a Wheatstone bridge-type of arrangement is connected to one or several piezoresistive elements provided on the membrane 10. As is well known in the art, a certain pressure exerted on the membrane 10 from the surrounding medium will thereby correspond to a certain stretching of the membrane 10 and thereby to a certain resistance of the piezoresistive elements mounted thereon and, in turn, to a certain output from the sensor element 8. It should therefore be clear that it is highly preferable that this output from the sensor element 8 does not change due to factors that are not related to a real change in the physical properties of the surrounding medium. As was mentioned above, one such factor is so-called bending artefacts, the source of which is that a bending of the sensor guide 1 is transferred to a deformation of the membrane 10. Here, the discussion above about piezoresistive elements coupled in a Wheatstone bridge-type of arrangement should only be seen as an illustrative exemplification; in short, the basic problem is that a pressure sensitive device, such as a membrane, can be influenced by a bending of a sensor guide.

To remedy the potentially adverse effects from bending artefacts, several different ways of mounting a sensor element are disclosed in U.S. Pat. Nos. 6,112,598 and 6,167,763, and in FIG. 2 one of these mounting arrangements is shown. FIG. 2 illustrates how the sensor chip 8, whose distal portion is provided with the membrane 10, is mounted on the core wire 3. The core wire 3 has been provided with a recess 12 that consists of two portions, a first portion having the purpose of a mounting shelf 13 for receiving the proximal portion of the chip 8 and a second portion 14, which is deeper than the first portion to allow the distal portion of the sensor chip 8 to protrude freely. The sensor chip 8 is thereby mounted in a cantilevering fashion, without the pressure sensitive distal end of the sensor chip 8 being in contact with any rigid structure. In this known design of a sensor guide, the sensor element 8 is disposed inside the jacket 6, and is through the electrical leads 9 in contact with an electronic unit (not shown in the figure).

Figure 4:
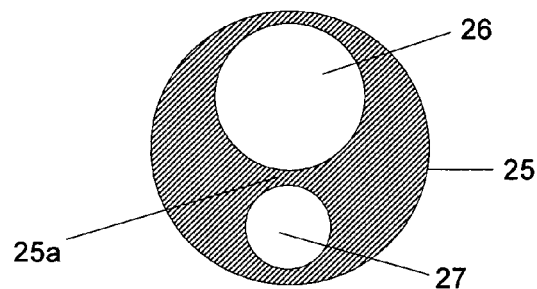
FIG. 4 shows the cross-section of the jacket of FIG. 3.

For the mounting arrangement shown in FIG. 2, as well as for the other mounting arrangements according to the prior art, it is the design of the sensor chip or the mounting arrangement, and in particular the design of the core wire, that provides the desired resistance against bending artefacts, while the jacket accommodating the sensor chip and the core wire in all cases has the same tubular shape. In contrast, FIG. 3 shows a portion of a sensor and guide wire assembly 20 according to the present invention. The sensor guide 20 comprises a core wire 21 and a sensor chip 22. A distal portion of the sensor chip 22 is provided with a pressure sensitive device in the form of a membrane 23, and a proximal portion of the sensor chip 22 is through at least one electrical lead 24 in contact with an electronic unit (not shown in the figure). The core wire 21 and the sensor chip 22 are arranged inside a jacket or sleeve 25, which—as is best seen in FIG. 4—comprises a first through hole or opening 26 and a second through hole or opening 27. The jacket 25 is made of a relatively rigid material such as stainless steel, as opposed to flexible material such as rubber. As is conventional in the art and like all embodiments to be described below, an aperture 28 is provided in the mantle wall of the jacket or sleeve 25. The pressure sensitive device 23 is through this aperture 28 in contact with the medium (e.g. blood) surrounding this portion of the sensor and guide wire assembly 20.

The jacket 25 is typically a few millimeters long. In some applications, the aperture 28 may be covered with a thin or highly flexible membrane (not shown).

At its proximal end the jacket 25 ends in a portion 29 having a smaller diameter than the main body of the jacket 25. This end portion 29 serves as a connection piece, to which a proximal coil 30 has been attached. A similar end portion or connection piece 31, having a smaller diameter than the main body of the jacket 25, is provided at the distal end of the jacket 25, and is adapted for attachment to a distal coil 32. The connection pieces 29, 31 are not crucial for the present invention, but since the jacket 25—because of the off-centre positioning of the second opening 27 in the jacket 25—is not coaxially arranged around the core wire 21, the connection pieces 29, 31 will ensure that the jacket 25 is centred with respect to the proximal and distal coils 30, 32, something that usually is advantageous.

During manufacturing of the sensor and guide wire 20 according to the present invention, the sensor chip 22 is positioned inside the first through hole 26, while the core wire 21 is threaded through the second through hole 27. The sensor can be fixated in the first hole 26 by means of, for example, gluing or soldering to the upper side of the jacket, or by filling the first through hole 26 with a suitable material such as silicone. The sensor chip 22 is thus not attached to the core wire 21 and does not touch the core wire 21. Likewise, the jacket or sleeve 25 can be attached to the core wire 21 by means of, for example, gluing or soldering, or by filling the second through hole 27 with a suitable material such as silicone. The dimensions of the openings 26, 27 in the jacket 25 can, however, also be closely adapted to the dimensions of the sensor chip 22 and the core wire 21, respectively, so that no extra measures have to be taken to fixate the sensor chip 22 and/or core wire 21.

By arranging the sensor chip 22 in a first through hole 26 and the core wire 21 in a second through hole 27, the sensor chip 22 is virtually independent of movements of the core wire 21; and in particular bending deformations of the core wire 21 will not be transferred to the sensor chip 22 and to the membrane 23.

Figure 5:
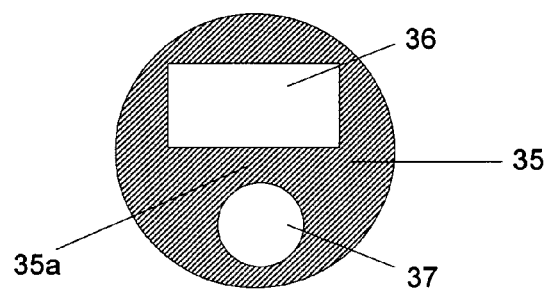
FIG. 5 shows the cross-section of a second embodiment of a jacket according to the present invention.

As was indicated above, the shape of a through opening in a jacket or sleeve can according to the present invention be adapted to the shape of the member to be positioned therein. FIG. 5 illustrates a second embodiment of a sleeve or jacket 35, in which two through openings 36, 37 have been created. Here the first through opening 36 has been given a rectangular cross-section, which is adapted to a rectangular cross-section of a sensor chip (not shown in the figure). Like the embodiment shown in FIG. 4, the second through opening 37 has been given a circular cross-section in order to fit to a circular cross-section of a core wire (not shown in the figure), but other cross-section configurations are also possible. A rectangular cross-section, adapted to a core wire having a corresponding cross-section, could, for example, be advantageous in that it would prevent the core wire from rotating inside the jacket.

Figure 6:
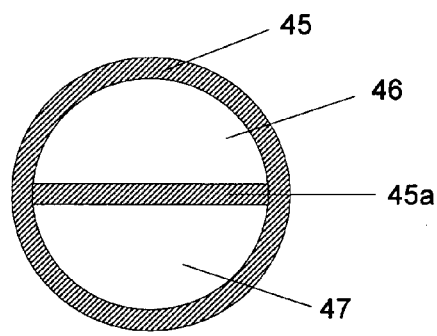
FIG. 6 shows the cross-section of a third embodiment of a jacket according to the present invention.

The through openings shown in FIGS. 4 and 5 are preferably made by drilling, punching or cutting holes in an otherwise solid cylindrical member, which can be made from any suitable material such as metal, plastic or ceramic. Another way of forming separate openings for a core wire and a sensor chip is illustrated in FIG. 6. Here a jacket or sleeve 45 comprises a first through opening 46, which is intended for accommodating a sensor chip (not shown in the figure), in the form of a semi-circular compartment and a second through opening 47, which is intended for accommodating a core wire (not shown in the figure), also in the form of a semi-circular compartment. The first and second through openings 46, 47 are separated by a partition wall 45a. In addition to the manufacturing techniques mentioned above, other ways of manufacturing a jacket or sleeve having two separate through holes may hereby be considered. For example, the jacket shown in FIG. 6 can be manufactured by providing a partition wall inside a hollow tubular member. The partition wall could then be glued or soldered to the inner wall of the tubular member 45. Furthermore, the interior of the tubular member could be divided into two separate compartments having different dimensions, such that each compartment would have a cross-section in the shape of the letter D, but where the two compartments would have different lengths of the straight portions. Like for the two previous embodiments, the space not occupied by the core wire or by the sensor chip could be filled with a suitable material, such as silicone. For example, the space for the sensor chip can be at least partially filled with an elastic compound such that the sensor chip or element floats in the elastic compound, to provide further protection from bending stress.

Figure 7:
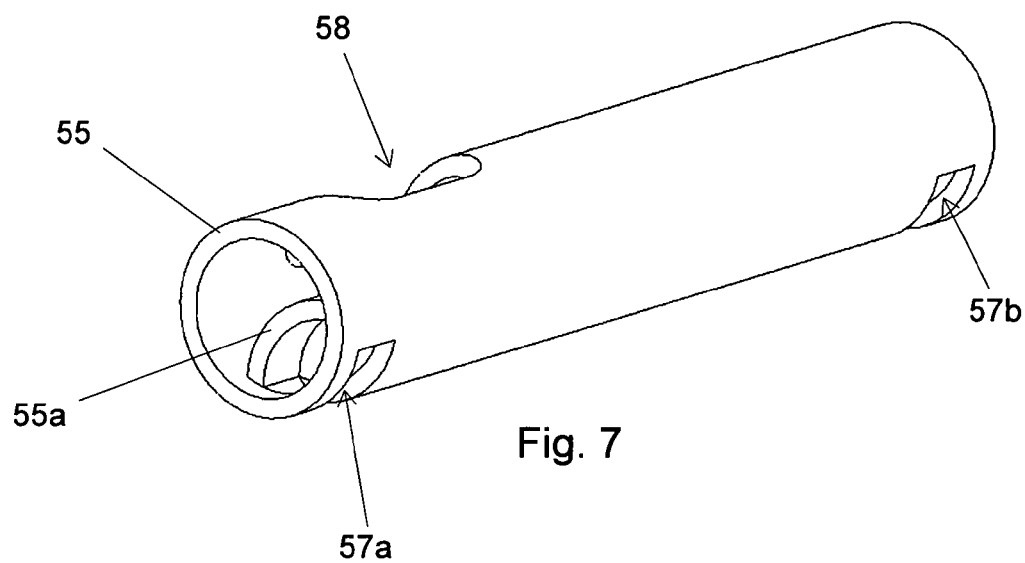
FIG. 7 is a perspective view of a fourth embodiment of a jacket according to the present invention.
Figure 8:
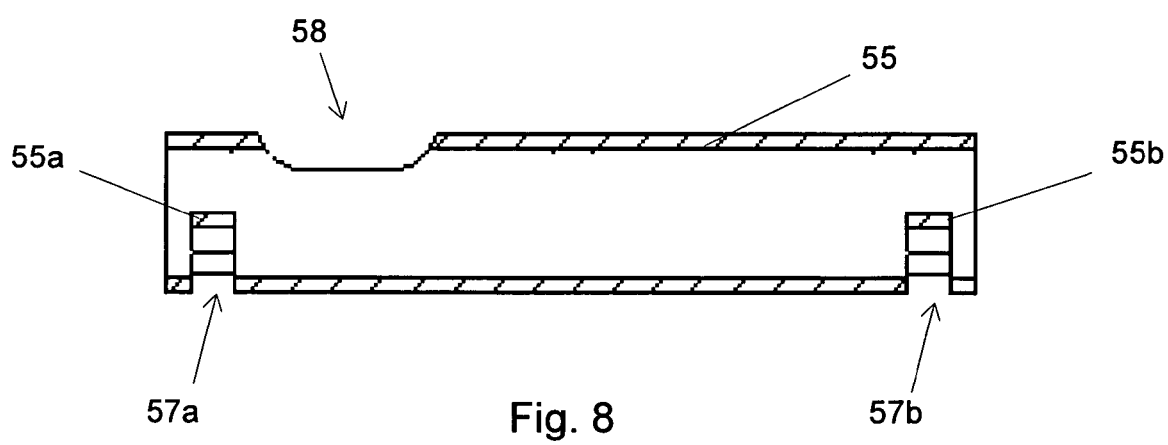
FIG. 8 is a cross-section of the fourth embodiment of a jacket according to the invention.

FIGS. 7 and 8 illustrate a jacket 55 according to a fourth embodiment of the present invention. This embodiment also includes an aperture 58 through which pressure may be sensed. This embodiment includes two crimps 57a and 57b in order to retain the core wire (not shown) in the lower portion of the jacket 55. Crimps 57a and 57b include members 55a and 55b, respectively, which protrude from the inner surface of the jacket into the central portion of the jacket in order to retain the core wire (not shown) in a location separate from the location of the sensor chip (not shown).

Figure 9:
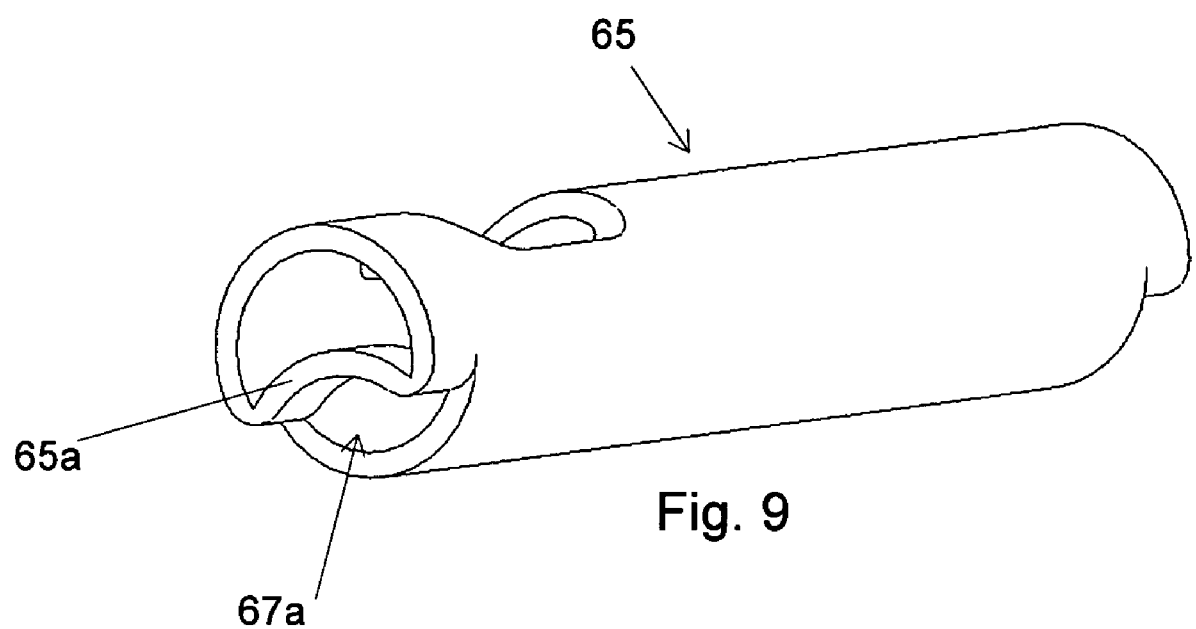
FIG. 9 is a perspective view of a fifth embodiment of a jacket according to the present invention.

FIG. 9 illustrates a jacket 65 according to a fifth embodiment of the present invention. This embodiment is a variation of the embodiment shown in FIGS. 7 and 8 and includes a crimp 67a at an end portion of the jacket 65. This embodiment also includes a member 65a which protrudes from an inner surface of the jacket toward a central portion of the jacket to retain the core wire (not shown) separate from the sensor chip (not shown).

Figure 10:
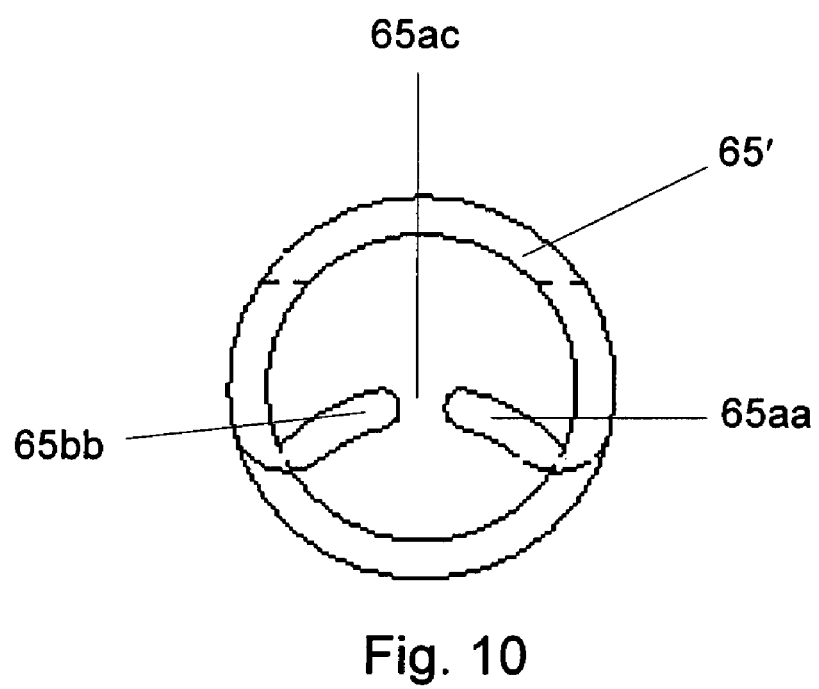
FIG. 10 is a cross-section of a sixth embodiment of a jacket according to the present invention.

FIG. 10 illustrates a jacket 65' according to a sixth embodiment of the present invention. In this embodiment 65', two members 65aa and 65bb protrude from an inner surface of the jacket toward a central portion of the jacket to retain the core wire (not shown) separate from the sensor chip (not shown). These two members are separated by a gap 65ac. It should be noted that the embodiments of FIGS. 3 to 6 are similar to the embodiments of FIGS. 7 to 10 in that the embodiments of FIGS. 3 to 6 also include at least one member 25a, 35a, and 45a which protrudes from an inner surface of the jacket toward a central portion of the jacket to retain the core wire (not shown) separate from the sensor chip (not shown).

Before ending the description of preferred embodiments of the present invention it should be mentioned that the two separate openings in a jacket (sleeve or tubular member), which have been described and illustrated as passing all the way through the sleeve (sometimes called through-and-through openings) actually could be closed at least one end. In particular for the sensor chip it is conceivable that the first opening on the distal side (the left hand side in FIG. 3) ends in a closed wall, so that the sensor chip only can be contacted from the proximal side. It is also possible to arrange the sensor chip in such a way that it is not completely enclosed by the jacket, e.g., by having a jacket whose length is shorter than the length of the sensor chip.

For the invention, the important feature is that a sensor chip is arranged within a first opening (which also could be referred to as a hole, compartment or cavity) in a jacket (sleeve or tube), and that a core wire is disposed within a second opening (which also could be referred to as a hole, compartment or cavity) in the jacket, such that the first and second openings are completely separated from each other (as in the embodiments shown in FIGS. 4–6), or such that the first and second openings are partially separated from each other in such a way that the sensor chip is separated from the core wire (as in the embodiments shown in FIGS. 7–10). With this arrangement, the sensor chip is essentially independent of movements of the core wire; and in particular bending deformations of the core wire will not be transferred to the sensor chip.

Although the present invention has been described with reference to specific embodiments, also shown in the appended drawings, it will be apparent for those skilled in the art that many variations and modifications can be done within the scope of the invention as described in the specification and defined with reference to the claims below. It should in particular be noted that the improved characteristics of a sensor guide provided with a jacket according to the invention are not dependent on the design of the other parts of the sensor guide. For example, the core wire, to which the jacket is attached, may extend along essentially all the length of the sensor guide, or the core wire may only be provided at the distal portion of the sensor guide.

What is claimed is:

1. A jacket for a sensor guide wire assembly for intravascular measurements of at least one physiological variable in a living body, which jacket is adapted to enclose a portion of a core wire and is adapted to accommodate at least a portion of a sensor chip, wherein the jacket comprises
    a first opening, which is adapted to accommodate said portion of the sensor chip,
    a second opening, which is adapted to accommodate said portion of the core wire, and
    at least one member protruding toward a central portion of the jacket to help retain the core wire separate from the sensor chip.

2. A jacket according to claim 1, wherein the first opening has a circular cross-section.

3. A jacket according to claim 1, wherein the first opening has a non-cylindrical cross section.

4. A jacket according to claim 1, wherein the cross-section of the first opening is adapted to the cross-section of the sensor chip.

5. A jacket according to claim 1, wherein the second opening has a circular cross-section.

6. A jacket according to claim 1, wherein the second opening has a non-circular cross-section.

7. A jacket according to claim 1, wherein the cross-section of the second opening is adapted to the cross-section of the core wire.

8. A jacket according to claim 1, wherein the jacket comprises a tubular member and the first and second openings are created by a partition wall arranged within the tubular member.

9. A jacket according to claim 1, wherein a proximal end portion of the jacket has a smaller diameter than a main portion of the jacket.

10. A jacket according to claim 9, wherein the diameter of the proximal end portion of the jacket is adapted to the inner diameter of a coil, which is to be attached to the proximal end portion of the jacket.

11. A jacket according to claim 1, wherein a distal end portion of the jacket has a smaller diameter than a main portion of the jacket.

12. A jacket according to claim 11, wherein the diameter of the distal end portion of the jacket is adapted to the inner diameter of a coil, which is to be attached to the distal end portion of the jacket.

13. A jacket according to claim 1, wherein at least one end portion of the first opening is closed.

14. A jacket according to claim 1, wherein at least one end portion of the second opening is closed.

15. A jacket according to claim 1, wherein the first and second openings are at least partially separated from each other.

16. A jacket according to claim 1, wherein said member is continuous from one side of the jacket to another side of the jacket.

17. A jacket according to claim 1, further comprising at least one additional member protruding toward the central portion of the jacket to help retain the core wire separate from the sensor chip, said at least one member and said at least one additional member being separated from each other by a gap.

18. A sensor guide wire assembly for intravascular measurements of at least one physiological variable in a living body, comprising
    a core wire,
    a sensor element, and
    a jacket,
    wherein the jacket comprises a first opening, in which at least a portion of the sensor element is arranged, and a second opening, in which at least a portion of the core wire is arranged, and further comprising
        at least one member protruding toward a central portion of the jacket to help retain the core wire separate from the sensor element.

19. A sensor guide wire assembly according to claim 18, wherein the first opening is filled with an elastic compound.

20. A sensor guide wire assembly according to claim 18, wherein the first opening is at least partially filled with an elastic compound and the sensor element floats in the elastic compound.

21. A sensor guide wire assembly for intravascular measurements of at least one physiological variable in a living body, comprising:
    a jacket adapted to enclose a portion of a core wire and adapted to accommodate at least a portion of a sensor chip,
    wherein
    the jacket includes a first opening which is adapted to accommodate said portion of the sensor chip and a second opening which is adapted to accommodate said portion of the core wire, and
    the jacket further includes at least one member protruding from an inner surface of the jacket toward a central portion of the jacket to help retain the core wire separate from the sensor chip.

22. An assembly according to claim 21, wherein said member is continuous from one side of the inner surface of the jacket to another side of the inner surface of the jacket.

23. A jacket for a sensor guide wire assembly for intravascular measurements of at least one physiological variable in a living body, which jacket is adapted to enclose a portion of a core wire and is adapted to accommodate at least a portion of a sensor chip, wherein the jacket comprises
    a first opening, which is adapted to accommodate said portion of the sensor chip;
    a second opening, which is adapted to accommodate said portion of the core wire; and
    at least one member protruding from an inner surface of the jacket toward a central portion of the jacket to help retain the core wire separate from the sensor chip.

* * * * *